(12) United States Patent
Rawson et al.

(10) Patent No.: US 8,030,068 B2
(45) Date of Patent: *Oct. 4, 2011

(54) METHOD FOR CULTURING MAMMALIAN TASTE CELLS

(75) Inventors: Nancy Ellen Rawson, Drexel Hill, PA (US); Mehmet Hakan Ozdener, Upper Darby, PA (US)

(73) Assignee: Monell Chemical Senses Center, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/348,274

(22) Filed: Jan. 2, 2009

(65) Prior Publication Data
US 2010/0190256 A1 Jul. 29, 2010

Related U.S. Application Data

(63) Continuation of application No. 11/249,854, filed on Oct. 13, 2005, now Pat. No. 7,488,599.

(60) Provisional application No. 60/636,377, filed on Oct. 15, 2004.

(51) Int. Cl.
C12N 5/00 (2006.01)
C12N 5/02 (2006.01)

(52) U.S. Cl. ......... 435/325; 435/381; 435/404; 435/371

(58) Field of Classification Search .................. None
See application file for complete search history.

(56) References Cited

U.S. PATENT DOCUMENTS
7,488,599 B2 * 2/2009 Rawson et al. ............... 435/325

FOREIGN PATENT DOCUMENTS
| | | |
|---|---|---|
| JP | 2002-165590 | 6/2002 |
| JP | 2003-102470 | 4/2003 |
| WO | WO 03/031604 | 4/2003 |
| WO | WO 2004/090122 | 10/2004 |

OTHER PUBLICATIONS

Nelson and Finger, The J Comp Neurology 336: 507-516, 1993.*
Ruiz et al., Tissue Culture of Rat Taste Buds, ed Spielman and Brand, Experimental Cell Biology of Taste and Olfaction 79-84, 1995.*
Ruiz et al., Chem Senses 26: 861-873, 2001.*
Kishi et al Neuroscience 106: 217-225, 2001.*
Miura et al Chem Senses 30: 367-375, 2005.*
Ookura et al., In Vitro Cell Dev Biol—Animal 38: 365-372, 2002.*
Uehara et al. J Gen Physiol 61: 290-304, 1973.*
Montmayeur et al Nat Neurosc 4: 492-498, 2001.*
Spielman et al (Brain Res 503: 326-329, 1989).*
Ozdener et al (Chem Senses 31: 279-290, 2006).*
Stone et al (Chem Senses 2: 779-787, 2002).*
Baumstark et al., "Purification of pancreatopeptidase E by batch separation on DEAE-cellulose", Biochim. Biophys. Acta., Nov. 8, 1963, 77, 676-679.
Bryant, "Trigeminal Nerve Recordings in Rodents", Experimental Cell Biology of Taste and Olfaction: Current Techniques and Protocols, Ed. Andrew I. Spielman, CRC Press, Boca Raton, Jul. 12, 1995, 271-276.
Bufe et al., "The human TAS2R16 receptor mediates bitter taste in response to .beta.-glucopyranosides", Nature Genetics, Nov. 2002, 32(3), 397-401.
U.S. Appl. No. 60/636,377, filed Oct. 15, 2004, Rawson et al.
Flegner "Cationic Liposome-Mediated Transfection with Lipofectin Reagent", Gene Transfer and Expression Protocols, Ed. E.J. Murray, Humana Press, NJ, (No Month Available) 1991, Chapter 8, 81-89.
Flegner et al., "Cationic Lipid-Mediated Transfection in Mammalian Cells: 'Lipofection'", Journal of Tissue Culture Methods, Jun. 1993, 15(2), 63-68.
Flegner et al., "Enhanced Gene Delivery and Mechanism Studies with a Novel Series of Cationic Lipid Formulations", Journal of Biological Chemistry, Jan. 28, 1994, 269(4), 2550-2561.
Frank "TasteNerve Recordings in Rodents", Experimental Cell Biology of Taste and Olfaction: Current Techniques and Protocols, Ed. Andrew I. Spielman, CRC Press, Boca Raton, Jul. 12, 1995, 263-270.
Frank et al., "Contemporary Measurement of Human Gustatory Function", Handbook of Olfaction and Gustation, Ed. Richard L. Doty, Marcel Dekker, Inc., NY, (No Month Available) 2003, 783-804.
Gilbertson et al., "Distribution of Gustatory Sensitivities in Rat Taste Cells: Whole-Cell Responses to Apical Chemical Stimulation", Journal of Neuroscience, Jul. 1, 2001, 21(13), 4931-4941.
Gilbertson, "Patch-Clamping of Taste Cells in Hamster and Rat", Experimental Cell Biology of Taste and Olfaction: Current Techniques and Protocols, Ed. Andrew I. Spielman, CRC Press, Boca Raton, Jul. 12, 1995, 317-328.
Hayashi et al., "Measurement of Membrane Potential and [Ca.sup.2+], in Cell Ensembles: Application to the Study of Glutamate Taste in Mice", Biophysical Journal, Aug. 7, 1996, 71(2), 1057-1070.
Heiner et al., "Expression profile of the transient receptor potential (TRP) family in neutrophil granulocytes: evidence for currents through long TRP channel 2 induces by ADP-ribose and NAD", Biochemical Journal, May 1, 2003, 371(Pt 3), 1045-1053.

(Continued)

*Primary Examiner* — Ali R. Salimi
*Assistant Examiner* — Aditi Dutt
(74) *Attorney, Agent, or Firm* — Woodcock Washburn LLP

(57) ABSTRACT

The invention provides methods of culturing mammalian taste cells, including taste receptor cells. Cells are maintained for a duration of up to three months and longer while maintaining molecular and functional characteristics of mature taste cells. The cells are cultured on coated cell culture vessels and, from first replacement of medium onwards, the medium is replaced in intervals of at least 5 days. The invention further provides isolation and culturing methods of taste cells wherein the time that the cells are exposed to isolation solution and proteolytic enzymes is minimized and the cells are cultured in coated culture vessels with the medium replaced in intervals of at least 5 days from first replacement onwards. The invention further provides cultured taste cells, transfection and assay methods, and taste cell assay buffers with an osmolarity of about 300-320 and pH of about 7.0-7.3.

8 Claims, No Drawings

OTHER PUBLICATIONS

Kishi et al., "Primary Culture of Rat Taste Bud Cells that Retain Molecular Markers for Taste Buds and Permit Functional Expression of Foreign Genes", Neuroscience, Sep. 3, 2001, 106(1), 217-225.

Landin et al., "Liposome-Mediated Transfection of Mature Taste Cells", Journal Neurobiology, Oct. 2005, 65(1), 12-21.

Medler et al. Electrophysiological Characterization of Voltage-Gated Currents in Defined Taste Cell Types of Mice, Journal of Neuroscience, Apr. 1, 2003, 23(7), 2608-2617.

Miura et al., "Temporal Changes in NCAM Immunoreactivity During Taste Cell Differentiation and Cell Lineage Relationships in Taste Buds", Chem. Senses, May 2005, 30(4), 367-375.

Miura, "Cell Lineage and Differentiation in Taste Buds", Arch Histol Cytol, Dec. 2006, 69(4), 209-225.

Nelson et al., "Immunolocalization of Different Forms of Neural Cell Adhesion Molecule (NCAM) in Rat Taste Buds", Journal of Comparative Neurology, Oct. 22, 1993, 336(4), 507-516.

Ogura et al., "Bitter Taste Transduction of Denatonium in the Mudpuppy Necturus maculosus", Journal of Neuroscience, May 15, 1997, 17(10), 3580-3587.

Okayama et al., "Calcium Phosphate Mediated Gene Transfer into Established Cell Lines", Gene Transfer and Expression Protocols, Ed. E.J. Murray, Humana Press, NJ, (No Month Available) 1991, 15-21.

Ookura et al., "Fibroblast and epidermal growth factors modulates proliferation and neural cell adhesion molecule expression in epithelial cells derived from the adult mouse tongue", Vitro Cellular & Developmental Biology Animal, Jun. 1, 2002, 38, 365-372.

Ozdener et al., "Characterization and Long-Term Maintenance of Rat Taste Cells in Culture", Chem. Senses, Feb. 1, 2006, 1-12.

Perkus et al., "Methodology of Using Vaccinia Virus to Express Foreign Genes in Tissue Culture", Journal of Tissue Culture Methods, Jun. 1993, 15(2), 72-81.

Perkus et al., "Poxvirus-based vaccine candidates for cancer, AIDS, and other infectious diseases", Journal of Leukocyte Biology, Jul. 1995, 58, 1-13.

Product Information Sheet, Sigma, Iscove's Medium, 2 pgs. (No Date Available).

Product Specification Sheet, Sigma, MCDB Medium, 2 pgs. (No Date Available).

Restrepo et al., "Imaging of Intracellular Calcium in Chemosensory Receptor Cells", Experimental Cell Biology of Taste and Olfaction: Current Techniques and Protocols, Ed. Andrew I. Spielman, CRC Press, Boca Raton, Jul. 12, 1995, 387-398.

Rossler et al., "G Protien .beta.y Complexes in Circumvallate Taste Cells Involved in Bitter Transduction", Chemical Senses, Aug. 2000, 25(4), 413-421.

Ruiz et al., "Maintenance of Rat Taste Buds in Primary Culture", Chem. Senses, Sep. 2001, 26(7), 861-873.

Ruiz et al., "Tissue Culture of Rat Taste Buds", Experimental Cell Biology of Taste and Olfaction: Current Techniques and Protocols, Ed. Andrew I. Spielman, CRC Press, Boca Raton, Jul. 12, 1995, 79-84.

Sambrook et al., "Expression of Cloned Genes in *Escherichia coli*", Molecular Cloning: A Laboratory Manual, Cold Spring Harbor Laboratory Press, NY, (No Month Available) 2001, 15.1-15.13.

Smith et al., "Expression of Neural Cell Adhesion Molecule (NCAM) and Polysialic Acid During Taste Bud Degeneration and Regeneration", Journal of Comparative Neurology, Sep. 8, 1994, 347(2), 187-196.

Spielman et al., "A method for isolating and patch-clamping single mammalian taste receptor cells", Brain Research, Dec. 4, 1989, 503(2), 326-329.

Stone et al., "Virus-mediated Transfer of Foreign DNA into Taste Receptor Cells", Chem. Senses, Nov. 2002, 27(9), 779-787.

Takeda et al., "Neural Cell Adhesion Molecule of Taste Buds", J. Electron Microsc., Oct. 1992, 41(5), 375-380.

Ueda et al., "Functional Interaction between T2R Taste Receptors and G-Protein .alpha. Subunits Expressed in Taste Receptor Cells", The Journal of Neuroscience, Aug. 13, 2003, 23(19), 7376-7380.

Yang et al., "Ultrastructural Localization of Gustducin Immunoreactivity in Microvilli of Type II Taste Cells in the Rat", Journal of Comparative Neurology, Sep. 11, 2000, 425(1), 139-151.

Yee et al., "'Type III' Cells of Rat Taste Buds: Immunohistochemical and Ultrastructural Studies of Neuron-Specific Enolase, Protein Gene Product 935, and Serotonin", Journal of Comparative Neurology, Nov. 5, 2001, 440(1), 97-108.

Zhang et al., "Reassembly of Phospholipase C-.beta..sub.2 from Separated Domains", Journal of Biological Chemistry, Jan. 26, 2001, 276(4), 2503-2508.

Zviman et al., "Single Taste Stimuli Elicit Either Increases or Decreases in Intracellular Calcium in Isolated Catfish Taste Cells", Journal of Membrane Biology, Jan. 1996, 149(2), 81-88.

Kawamoto et al., "Establishment and Characterization of a Cell Line Derived From Mouse Tongue Epithelium Cells", Japanese Journal of Taste and Smell Research, 2002, 9(3), 513-514, With English Translation Attached.

\* cited by examiner

SEQUENCE LISTING

```
<160> NUMBER OF SEQ ID NOS: 12

<210> SEQ ID NO 1
<211> LENGTH: 29
<212> TYPE: DNA
<213> ORGANISM: Artificial Sequence
<220> FEATURE:
<223> OTHER INFORMATION: primer

<400> SEQUENCE: 1
gatgctagcc aatccgagaa gtagagagg                                        29

<210> SEQ ID NO 2
<211> LENGTH: 29
<212> TYPE: DNA
<213> ORGANISM: Artificial Sequence
<220> FEATURE:
<223> OTHER INFORMATION: primer

<400> SEQUENCE: 2
cggagatctg ctgttgaaga ggtgaagac                                        29

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
ctggaggctg aagtaaagga g                                                21

<210> SEQ ID NO 4
<211> LENGTH: 20
<212> TYPE: DNA
```

```
<213> ORGANISM: Artificial Sequence
<220> FEATURE:
<223> OTHER INFORMATION: primer

<400> SEQUENCE: 4
gcccctgcat gtatgttagg                                                    20

<210> SEQ ID NO 5
<211> LENGTH: 19
<212> TYPE: DNA
<213> ORGANISM: Artificial Sequence
<220> FEATURE:
<223> OTHER INFORMATION: primer

<400> SEQUENCE: 5
tcatgtttga gaccttcaa                                                     19

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6
gtcttgcgga tgtccacg                                                      18

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
tggcaaatcc acatgaagaa                                                    20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
gcagggatag aggaatgcaa                                                    20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
gatcagtggt ccccagaaaa                                                    20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
taagctagca tggcgaaggt                                                    20
```

```
<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
caagatcatc gtggtagagc                                              20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
tccagaacat gtctgcgttg                                              20
```

METHOD FOR CULTURING MAMMALIAN TASTE CELLS

CROSS REFERENCE TO RELATED APPLICATIONS

The present application is a continuation of U.S. Ser. No. 11/249,854, filed Oct. 13, 2005, now U.S. Pat. No. 7,488,599, which claims the benefit of the filing date under 35 USC §119(e) of U.S. Provisional Application for Patent Ser. No. 60/636,377 filed Oct. 15, 2004, both of which are incorporated herein by reference.

FIELD OF THE INVENTION

The invention is concerned with methods for the isolation and long-term cell culture of mammalian taste cells. Mammalian taste cells include mammalian taste receptor-expressing cells that respond to taste stimuli or tastants. The methods of the invention allow the study of taste receptor cells for an extended period of time, for example up to three months or longer. Additionally, the methods of the invention reduce the number of animals from which taste cells need to be isolated compared to known methods. Since the methods of the invention allow taste cells to proliferate and differentiate in vitro, in vitro study of taste cell processes including proliferation and differentiation, for example the determination of trophic factors required by these processes, is made possible. The ability to culture taste cells for an extended period enables experiments requiring a longer timeframe.

BACKGROUND

The taste bud consists of approximately 50-100 taste cells which include three morphologic types that exhibit both neuronal and epithelial properties. Based on immunocytochemical characteristics, these taste cells can be classified as type I (dark), type II (light), and type III (intermediate) (Yee et al., *J Comp Neurol.* 2001 Nov. 5; 440 (1):97-108; Takeda et al., *J Comp Neurol.* 2004 Nov. 1; 479 (1):94-102).

Studies indicate that approximately 10% of these taste cells exhibit immunoreactivity for neural cell adhesion molecule (NCAM). While NCAM-immunoreactive cells are type III cells, not all type III taste cells are immunoreactive for NCAM (Nelson and Finger 1993, *J. Comp Neurol* 336 (4): 507-16), and NCAM expression in taste cells is dependent upon innervation by the IX nerve (Smith et al. 1994, *J. Comp Neurol* 347 (2):187-96). These and other data suggest that the NCAM-expressing taste cells communicate with nerves.

In contrast, key molecules required for functional responses to taste stimuli are not expressed in NCAM-immunoreactive cells. For instance, gustducin, is a key G-protein involved in taste transduction and is only present in type II cells. However, gustducin is not detected in NCAM-expressing cells. (Takeda et al. 1992, *J. Electron Microsc.* 41 (5):375-80; Yang et al. 2000, *J. Comp Neural* 425 (1):139-51).

Taste cells are believed to originate from the epithelial cell lineage with a limited average life span of 10 days, with dying cells being replaced by the basal cell population. The large majority of primary cell cultures of taste cells are reported to last a few days at best, e.g. 3 to 5 days maximum (compare, for example, for mouse taste cells a method modified from the isolation of mammalian central neurons by Spielman et al. 1989, *Brain Research* 503: 326-29; and for rat taste cells Kishi et al. 2001, *Neuroscience* 106 (1): 217-25, and Stone et al. 2002, *Chem. Senses* 27: 779-87).

To be able to detect a given tastant, taste cells typically need both the relevant taste receptor for the tastant (e.g., bitter, sweet, umami) and the molecules necessary for taste transduction. Taste receptors may include one or more of T2Rs and/or one or more of T1Rs. Signal transduction molecules may include gustducin and phospholipase C. Cells that express at least one taste receptor and are able to respond to at least one taste stimulus/tastant are referred to herein as "taste receptor cells." Taste cells thus comprise taste receptor cells among other cell types.

To date, there is no cell culture model for taste receptor cells and any in vitro research has had to rely on primary cell cultures of taste cells that are maintained for a limited time.

Ookura et al. (2002, *In Vitro Cell. Dev. Biol.-Animal* 38: 365-72) describe a particular type of cells isolated from mouse taste epithelium that have been sorted based on their integrin β1 marker and that express the NCAM marker. Thus, this integrin-positive continuous mouse cell culture does not generate cells similar to those responsible for the primary detection of taste stimuli.

Ruiz et al. (2001, *Chem. Senses* 26 (7):861-73) report the maintenance of primary cell cultures derived from taste buds for up to 14 days, provided the cells are kept at room temperature, which is believed to slow down various cellular processes. Notably, cells kept at 37° C. could be maintained only for a few days, as had been previously reported. The cells kept at room temperature are reported to start dying at around day 10, which corresponds to the expected average life span of taste cells. A protocol published by Ruiz et al. 1995 ("Tissue Culture of Rat Taste Buds", Eds Spielman A I, Brand J G Experimental Cell Biology of Taste and Olfaction, CRC Press, 1995) discloses a similar method at room temperature that mentions a culture duration of up to 18 days.

SUMMARY

The invention is generally directed to methods of isolation, culture, and/or assay of mammalian taste cells, including taste receptor cells, and to cultured mammalian taste cells.

Encompassed within the invention are methods of culturing mammalian taste cells by culturing taste cells in an appropriate cell culture medium and on (wherein the term "on" in the context of a culture vessel includes therein) a coated cell culture vessel and, from first replacement of medium onwards, replacing the medium at intervals of at least about 5 days. In some embodiments, the taste cells comprise taste receptor cells. In some embodiments, the taste cell comprise only taste receptor cells. In preferred embodiments, the cell culture medium comprises Iscove's medium comprising 15-20% MCDB 153, 10% FBS, 10 ng/ml insulin, and antibiotics. The coating of the culture vessel preferably comprises collagen.

Also encompassed by the invention are methods of isolating and culturing mammalian taste cells by isolating tongue epithelium wherein length of exposure of taste cells in the tongue epithelium to isolation solution in the presence or absence of proteolytic enzymes is minimized, incubating isolated taste cell epithelium pieces in an appropriate cell culture medium and on a coated cell culture vessel, and, from first replacement of medium onwards, replacing the medium at intervals of at least 5 days. The length of exposure of taste cells to isolation solution with or without proteolytic enzymes is about 30 minutes or less. In some embodiments, the taste cells comprise taste receptor cells, and in some embodiments, the taste cells comprise only taste receptor cells. In preferred embodiments, the cell culture medium comprises Iscove's medium comprising MCDB 153, FBS, insulin, and antibiotics. In more preferred embodiments, the cell culture medium comprises Iscove's medium comprising 15-20% MCDB 153, 10% FBS, 10 ng/ml insulin, and antibiotics. The coating of the culture vessel preferably comprises collagen.

Further contemplated by the invention are taste cells cultured or isolated and cultured according to the inventive methods. In preferred embodiments, the taste cell is a taste receptor cell. The taste receptor cell preferably responds to at least one taste stimulus. The cultured taste cells of the invention may be cultured for at least about 10 days at about 37° C. and at least about 20 days at about 18-37° C. The invention also encompasses cultures of the taste cells. In some preferred embodiments, the invention provides mammalian taste receptor cells that divide in cell culture for more than 48 hours, preferably for more than about 5 days, and more preferably for more than about 2 weeks.

The invention also provides a taste cell assay buffer having an osmolarity of about 300-320 milliosmol and a pH of about 7.0 to about 7.3 and methods of maintaining taste cells in such a buffer.

Transfected cultured mammalian taste cells are further contemplated. The transfected cells of the invention may be transfected with vector DNA, such as plasmid or viral vector DNA. Also provided are methods of transfecting cultured taste cells by contacting cultured mammalian taste cells with nucleic acids, such as but not limited to, vector DNA, for example, viral vector DNA or plasmid vector DNA.

Assay methods using the cultured mammalian taste cells are also encompassed by the invention. In some preferred embodiments, the taste cell assay buffer used in the assay methods has an osmolarity of 300-320 milliosmol and a pH of 7.0 to 7.3.

Methods for assessing taste response to a candidate taste stimulus by exposing a cultured taste cell to the candidate taste stimulus, and comparing one or more cellular responses of the taste cell to the candidate taste stimulus with responses of a cultured taste cell to a standard taste stimulus, wherein the same cellular response by a cultured taste cell to the candidate taste stimulus as to the standard taste stimulus indicates that the candidate taste stimulus causes the same taste response in taste cells as the standard taste stimulus, are provided. Also provided are methods for assessing taste response of a candidate taste cell comprising exposing a candidate cultured taste cell to a known taste stimulus, and comparing the cellular response of the candidate cultured taste cell to the cellular response of a standard taste cell to the known taste stimulus, wherein the same cellular response of the candidate taste cell as that of the standard taste cell to the known taste stimulus indicates that the candidate taste cell shares the response of the standard taste cell to the taste stimulus.

Further provided herein are methods for identifying a taste modifier by exposing a cultured taste cell to the candidate taste modifier in the presence of a known taste stimulus, and comparing one or more cellular responses of the taste cell to the candidate taste modifier to the cellular responses in the absence of the candidate modifier, wherein a change in the cellular responses to the stimulus in the presence of the candidate modifier is indicative of a taste modifier.

Other features and advantages of the invention will be apparent from the detailed description and examples that follow.

DETAILED DESCRIPTION

Provided herein are isolation and culture methods that provide for the culture of taste cells, including taste receptor cells, for up to 1, 2, or 3 months, or longer. The methods of the invention retain a high percentage of viable cells, even at a temperature of 37° C. and consequently without slowing down all cellular processes.

The taste cell isolation and/or culture methods of the invention preferably include at least one of the following steps:

During isolation, the time that the taste cells are exposed to isolation solution, both with and without enzyme(s), is minimized. For example, taste cells are preferably not exposed to isolation solution for longer than about 30 minutes, preferably not longer than about 20 minutes, and most preferably not longer than about 15 minutes. For example, taste cells are preferably exposed to isolation solution employed as described below with pronase E and elastase not longer than about 30 minutes, preferably not longer than about 20 minutes, and most preferably not longer than about 15 minutes.

The cell culture vessel is coated with an appropriate coating. An appropriate coating for purposes of the invention is a coating that produces cell adhesion and proliferation. The coating preferably comprises collagen. The coating preferably does not comprise poly-D-lysine, CELL-TAK™, or MATRIGEL™.

An appropriate culture medium is used. An appropriate culture medium for purposes of the invention is a culture medium that supports cell viability, proliferation, and differentiation. A preferable culture medium for the methods of the invention comprises Iscove's Medium, MCDB 153, FBS, insulin, and antibiotics An example of an appropriate culture medium is Iscove's Medium with 15-20% MCDB 153, 10% FBS, 10 ng/ml Insulin and antibiotics. The culture medium preferably is not selected from DMEM, F12 or MCDB153, either alone or with fetal bovine serum (FBS) and antibiotic supplements.

Subsequent to the first replacement of medium (e.g., subsequent to the first replacement of culture medium at 24 to 48 hours), the medium should not be replaced at intervals shorter than about 5 days, preferably not less than about 7 days, and most preferably not less than about 8 days.

The methods of the invention preferably comprise two or more of these steps, more preferably three of more of these steps, and most preferably comprise all four of the steps.

Taste cell culture methods comprising one or more of these steps will provide a viability of taste cells of at least about 40%, preferably at least about 60%, most preferably at least about 75% after a culture duration of at least about 10 days at about 37° C., or at least about 20 days at about 18° C. to about 37° C. The taste cell culture methods preferably provide a viability of at least about 40%, preferably at least about 60%, and most preferably at least about 75% after a culture duration of about 1 to 2 months or longer at temperatures up to about 37° C. Cell viability may be tested by the Trypan Blue test described below.

Isolation and culture methods comprising each of the four steps achieve a viability of taste cells of at least about 80% to bout 90% or higher after a culture duration of at least about 10 days at about 37° C., or at least about 20 days at about 18° C. to 37° C. A culture method comprising each of the four steps preferably achieves a viability of at least about 80%, preferably about 90%, more preferably about 95%, and more preferably about 98% or higher after a culture duration of at least about one month at temperatures up to about 37° C.

The methods of the invention include methods for isolating and culturing mammalian taste cells comprising:
i) isolating tongue epithelium wherein the time that the cells are exposed to the isolation solution with or without enzyme(s) is minimized,
ii) incubating isolated tongue epithelium in an appropriate cell culture medium in a cell culture vessel coated with an appropriate coating, and
iii) subsequent to the first replacement of culture medium, for example at about 24-48 hours, replacing the medium at intervals of at least about 5 days.

In some preferred embodiments, the taste cells comprise taste receptor cells. In preferred embodiments, the taste cells comprise only taste receptor cells. In some embodiments, the time of exposure of the taste cells to isolation solution with or without enzyme(s) is about 30 minutes or less, more preferably about 20 minutes or less, and most preferably about 15 minutes or less. In some preferred embodiments, the coating is collagen. In some embodiments, the interval between culture medium replacement is at least about 7 days and preferably is at least about 8 days.

According to the methods of the invention, it is possible to maintain taste cells with a viability of at least about 40% for at least about 10 days at a temperature of up to about 37° C., or at least about 20 days at about 18° C. to about 37° C. In some embodiments, viability of at least about 80%, more preferably at least about 90%, even more preferably at least about 95%, for at least about 10 days at a temperature of up to about 37° C., or at least about 20 days at about 18° C. to about 37° C. is achieved according to the methods of the invention.

It has been found that taste cells attach particularly well to a coated surface. The invention thus also provides methods of culturing mammalian taste cells comprising
i) culturing taste cells in an appropriate cell culture medium in a coated cell culture vessel, and
ii) subsequent to the first replacement of culture medium, for example at about 24-48 hours, replacing the medium at intervals of at least about 5 days.

Taste cells cultured according to the methods of the invention may be isolated according to methods known in the art. Preferably, taste cells are isolated according to the methods provided herein. In some preferred embodiments, the taste cells comprise taste receptor cells. In some preferred embodiments, the coating is collagen. In some embodiments, the interval between culture medium replacement is at least about 7 days and preferably is at least about 8 days.

The invention also provides methods of maintaining taste cells for at least about 6 hours, preferably at least about 12 hours, and more preferably at least about 24 hours, in an improved assay buffer. The improved assay buffer has a defined osmolarity of about 300-320 milliosmol, preferably 300-310 milliosmol. The osmolarity of the assay buffer may be adjusted, for example with 5 M NaCl. A too high osmolarity, for example above about 320 milliosmol, is to be avoided as cells start to die and do not accept assay reagents such as fura-2 AM for the calcium imaging assay when determining the response of cells to taste stimuli (see, for example, Example 9). The assay buffer has a pH of about 7.0-7.3. A preferred pH for the improved assay buffer is about 7.15 to about 7.25. As a basis buffer, any suitable buffer may be used. If necessary, the basis buffer may be adjusted in osmolarity and/or pH. A suitable basis buffer is, for example, modified MHNK ringer's solution (80 mM NaCl, 5 mM KCl, 1 mM $MgCl_2$, 1 mM $CaCl_2$, 1 mM Na-pyruvate, 20 mM Hepes-Na, pH 7.2). The maintenance methods are useful when cells are to be maintained for assay purposes. None of the prior art methods were able to maintain taste cells including taste receptor cells in buffer solution for a comparable duration in buffer solution while maintaining responsiveness to taste stimuli.

Analysis of taste cells cultured according to the present invention shows that they maintain several functional and molecular properties throughout the culture duration, for example up to about one, two, or three months, or longer. In particular, cells continue to divide (as shown by BrdU labelling) and to differentiate into cells expressing taste receptor cell-specific markers, including gustducin, phospholipase C-beta-2 (PLC-β2), TRPM5, T1R3, and T2R5. Further, taste cells cultured according to the methods of the invention maintain the ability to be activated by taste stimuli. For example, taste cells cultured according to the methods of the invention are activated by one or more taste stimulants including Denatonium (Denatonium benzoate), Acesulfame K (6-Methyl-1,2,3-oxathiazin-4(3H)-one 2,2-dioxide potassium salt), MSG (Monosodium glutamate), Cycloheximide (3-[2-(3,5-Dimethyl-2-oxocyclohexyl)-2-hydroxyethyl]glutarimide), Glycine, and High K buffer (High K buffer is rich in potassium and contains a modified Modified MHNK ringer's solution with 5 mM NaCl, 80 mM KCl, 1 mM $MgCl_2$, 1 mM $CaCl_2$, 1 mM Na-pyruvate, and 20 mM Hepes-Na, pH 7.2 with osmolarity adjusted to 300-310 by 5M NaCl; All other stimulants are commercially available from Sigma, Saint Louis, Mo., USA) as shown by calcium imaging. Calcium imaging detects the elevation of intracellular calcium in response to activation by taste stimuli, which is one of several mechanisms of reaction to taste stimuli (entry of calcium from outside or release from internal calcium stores).

The invention also provides taste cells, including taste receptor cells, that continue to divide in cell culture for more than about 48 hours. Depending on culture duration, taste cells may continue to divide for more than about 5 days, preferably more than about 2 weeks, and more preferably more than about 4 weeks or longer. Notably, prior art methods provided taste cell cultures where either cell division continues only for a short period immediately following isolation or slows down so much that the cells do not survive but for a few days. Ruiz et al. 2001, supra, report that the addition of BrdU to cells already in culture for 48 hours resulted in essentially no labelling by BrdU. Whether cells continuously divide in culture can be easily tested using BrdU labelling, as is well-known in the art, for example after at least 2 days of culture. Taste cells according to the invention show a high percentage of BrdU-labelled cells, for example at least about 30% of cells. Preferably, at least about 40% of cells, more preferably about 50% of cells, even more preferably about 60% of cells, and most preferably at least about 70% of cells are BrdU-labelled. Usually, at least about 60-70% of cells are labelled.

Mammalian Taste Cells

Isolated taste papillae described in the examples are derived from tongues of rats, but material from other mammals may also be employed according to the methods of the present invention. All mammals share a high similarity in the organization of taste cells in the taste bud and in their cellular and molecular organization. Accordingly, taste cells of other mammals may also be isolated and/or cultured long-term with a similar viability. For example, common research animals that may be employed are rodents including for example, rat, mouse, hamster, and guinea pie. Other mammals that may be employed include, for example, bovine animals, pig, dog, cat, and primate (e.g., ape, monkey, human).

Methods of Taste Cell Isolation

Provided the incubation times with enzymes and isolation solution are short isolation methods for isolating tongue epithelial tissue and taste buds may be performed as is well known in the art. The original method was described by Spielman et al. 1989, *Brain Research* 503: 26-29. Various modifications of this method are known, as described for example by Kishi et al. 2001, *Neuroscience* 106 (1): 217-25. Stone et al. 2002, *Chem. Senses* 27: 779-87, and Ruiz et al. 2001, *Chem. Senses*. 26 (7):861-73.

The isolation procedure according to the invention involves incubation periods for the incubation in isolation solution and the incubation with proteolytic enzymes that are sufficiently short so that the desired duration of cultivation and cell viability is reached, which may be easily tested as described herein. Preferably, the duration of incubation both with isolation solution and proteolytic enzymes is about 30 minutes or less, preferably about 20 minutes or less, and more preferably about 15 minutes or less. The present invention employs a single isolation solution with an incubation of about 2 to about 1 minutes without enzymes, preferably on ice, to which one or more proteolytic enzymes are added and incubated about 10 to about 15 minutes.

Enzymes preferred for use in the isolation methods according to the invention are proteases that hydrolyze proteins sufficiently to separate taste cells in a short period of time not longer than about 30 minutes so that cells can be separated without damaging their ability to attach, grow, and differentiate. Suitable hydrolytic enzymes are, for example, pronase E and/or elastase. Preferably, more than one enzyme is used. For example, a combination of pronase E and elastase can be used in the isolation methods of the invention. Pronase E is a non-specific protease mixture from *Streptomyces griseus* and is commercially available, for example from Sigma, Saint Louis, Mo., USA. Elastase, for example pancreatic porcine elastase type I (synonyms: pancreatopeptidase E, Elastase hog pancreas. CAS number 39445-21-1: Enzyme Commission (EC) Number 3.4.21.36), hydrolyzes proteins including elastin with a preferential cleavage site of Ala-Xaa, and is commercially available from Sigma, Saint Louis, Mo., USA (for example 1 mg/ml elastase in aqueous suspension, 4 units mg protein. Product No. E1250).

Alternatively, the enzymes may be cloned and expressed as is well-known in the art and described for example by Baumstark et al. 1963, *Biochim. Biophys. Acta* 676; and Maniatis et al., 1982, "Molecular Cloning, A laboratory Manual", Cold Spring Harbor Laboratory.

The tongue epithelium is preferably minced following its isolation. Preferably, after the isolated epithelium from the region of the taste papillae (one or more of circumvallate, foliate, and fungiform papillae) is transferred to the culture vessel with medium, the isolated epithelium is minced using appropriate tools, for example surgical blades, to provide a mixture that comprises intact taste buds as well as partially dissociated taste buds. Primary cell cultures derived from such a mixture tend to provide cell cultures that can be kept over a longer period in time, which may be due to better attachment and/or longer periods of survival and/or growth.

Methods of Taste Cell Culture

Appropriate culture medium to be employed in the methods of the invention will support viability, proliferation, and differentiation of taste cells. Culture medium for the methods of the invention preferably comprises Iscove's medium, preferably supplemented with one or more of MCDB 153 medium, FBS, insulin, and antibiotics. A preferred medium for cell culture is for example Iscove's medium, preferably supplemented with one or more of 15-20% MCDB 153 medium, 5-20% FBS, 10 ng/ml insulin, and antibiotics. A suitable FBS concentration is 10%. A suitable combination of antibiotics is, for example, penicillin, streptomycin, gentamycin and fungizone. A suitable concentration is 100 U/ml/ 100 µg/ml, penicillin/Streptomycin, 2.5 µg/ml Gentamycin, and 0.5 µg/ml Fungizone.

Iscove's medium is a highly enriched synthetic medium modified from Dulbecco's Modified Eagle's medium (DMEM) and contains sodium selenite, additional amino acids and vitamins, sodium pyruvate, HEPES buffer and potassium nitrate instead of ferric nitrate. Iscove's medium is commercially available for example as "Iscove's Modification of DMEM" from Cellgro® by Mediatech Inc, Herndon, Va., USA (Product No. 10-016).

MCDB 153 medium, for example with L-Glutamine and 28 mM HEPES, without Sodium Bicarbonate, is a modification of Ham's nutrient mixture F-12 and is a highly enriched medium designed for serum-free growth and uses hormones, growth factors, trace elements or low levels of dialysed fetal bovine serum protein. MCDB 153 is commercially available from Sigma, Saint Louis, Mo., USA (Product No. M 7403).

An appropriate temperature for cell culture is any temperature that allows for cell growth and cellular processes at the desired rate, for example about 18° C. to about 37° C., including room temperature (18-22° C.) and about 37° C., for example 35 to 39° C. A preferred temperature is 37° C. which is physiological temperature and provides for cellular processes at their usual rate. When culturing cells for example at about 37° C., temperature will change over time somewhat to oscillate around 37° C. on average, e.g. ±0.5 or 1° C. depending on the cell culture system, as is apparent to the skilled person.

Cell culture is performed in an appropriate environment with appropriate $CO_2$ concentration and appropriate humidity, as is apparent to the skilled person. For example, depending on the buffer system of the chosen medium, a $CO_2$ concentration of about 5% is appropriate. Cells are usually cultured under conditions of high humidity, for example about 95%. Cell culture vessels, for example dishes or cover slips, according to the invention are coated, preferably with collagen, more preferably type I collagen, and most preferably rat tail type I collagen.

After the first medium replacement which may occur, for example, about 24-48 hours after seeding, any subsequent medium replacement is performed in intervals not shorter than at least about 5 days, preferably at least about 7 days, and most preferably at least about 8 days. Depending on culture conditions, chosen medium, concentration of antibiotics, and growth rate, after about 10 days, the medium generally should be replaced.

Any method known in the art may be used to assess cell viability. For example, Trypan Blue staining (Sigma, Saint Louis, Mo., USA) may be employed. Viability may be tested as follows: Trypan Blue (Sigma, Saint Louis, Mo., USA) is added directly to the cell culture medium of the culture vessel to give a concentration of 0.2% (w/v) Trypan Blue. Trypan Blue stains the cell nuclei of dead cells blue. After 5 to 10 minutes, 100 cells are counted under a phase contrast microscope at 10× magnification using an ocular grid. Viability is determined as a percentage (viable cells counted divided by total cells counted, multiplied by 100). The procedure is repeated % with 2-3 coverslips and the average determined. Variation between different coverslips is generally low. Cell cultures are at least about 80% viable, more preferably at least about 80% viable, more preferably at least about 90% viable, more preferably at least about 95%, even more preferably at least about 98%, and even more preferably at least about 99% viable).

Taste Cell Assays

Methods and taste cells according to the invention may be used in assay methods known in the art to identify candidate stimuli or compounds that elicit a response in taste cells, including tastants, taste modifiers (including stimuli that enhance, suppress, stimulate or inhibit taste, or influence a particular taste quality), and other candidate stimuli or compounds that elicit a particular response or effect in taste cells. For example, these assays may be used to identify and evaluate the taste, taste quality, taste modifying, growth promoting, inhibiting or toxic effects of candidates. Further they may be employed to identify candidates for treating taste loss, targets for drug development, and nutritional factors needed for maintenance of healthy taste cells. In general, such assays involve the comparison of at least one type of cellular response (e.g. fluorescent signal relating to calcium concentration) of a candidate or mixture of candidates of interest to a standard.

A candidate stimulus or compound may be, for example a candidate tastant or a candidate taste modifier in presence of a tastant. A standard stimulus or compound may be a known taste stimulus or tastant of a known taste quality, or a stimulus/compound that is able to elicit a particular effect on taste cells. Such an effect may be a growth promoting, inhibiting, or toxic effect, or the loss of response to taste stimuli, the maintenance of cell growth or health of taste cells. The candidate and the standard may be the same (for example a known tastant) if differences in the response of different taste cells, e.g. taste cells of different sources (species, individuals, age, etc.) are to be compared.

Taste cells including taste receptor cells according to the invention are exposed to the candidate and standard and the cellular response that results in a measurable signal is compared. Exposure may be done consecutively or in parallel as is well known in the art. Several stimuli or compounds may be tested together.

Different cellular responses are well known in the art and include changes in the calcium concentration, pH, and voltage. Changes of the response may involve changes in magnitude, latency (defined as the time between stimulus exposure and response) or duration. These changes may be detected by detection methods well-known in the art including fluorescent compounds sensitive to calcium or pH, voltage sensitive dyes (for example as described by Hayashi et al. 1996, *Biophys J.*, 71 (2):1057-70), and electrophysiological recording (for example as described by Ogura et al., *J Neurosci.* 1997 May 15; 17 (10):3580-7, and Zviman M M et al., *J Membr Biol.* 1996 January: 149 (2):81-8).

There is a large variety of specific assay types and it is apparent to the skilled person how to set them up in detail. For example, an assay may be performed as described by Frank M E, "Taste nerve recording in rodents", In: "Experimental cell biology of taste and olfaction", Ed by A. Spielman and J. Brand, CRC Press, 1995; Bryant, B P, "Trigeminal nerve recording in rodents", Ed by A. Spielman and J. Brand, CRC Press, 1995; Gilbertson T A, "Patch-clamping of taste cells in hamster and rat", Ed by A. Spielman and J. Brand. CRC Press, 1995.

An overview of some functional assays is provided herein.

Tastant Identification/Characterization Assay:

Taste cell response to a candidate of unknown taste quality is compared with that of a known tastant to identify differences or similarities in the cellular response. Taste cells are identified by their response to a known tastant, for example as described in Example 8 or using comparable cellular response assays known to the skilled person. The cellular response to the candidate is monitored and compared to the cellular response of the same cells to the tastant.

Modifier (Taste Modifier) Assay:

Taste cell responses to a known stimulus (e.g. known tastant) in the presence and in the absence of a candidate modifier (e.g. taste modifier) are compared. Cellular responses are detected and compared. Comparison may show that the response is increased, decreased, delayed, prolonged, or unaffected. A candidate modifier producing an increase in the magnitude of the cellular response to the stimulus or an increase in the frequency of cells responding to the stimulus shows that the candidate modifier is useful for enhancing the intensity of the stimulus (e.g. tastant), and may be useful to add to certain products such as food products, to enhance the given stimulus (e.g. taste stimulus/flavor). A stimulus or compound producing a response of shorter latency or longer response duration indicates an increased intensity or altered quality.

Findings of an elevated taste intensity, or a faster or more prolonged taste perception identify a stimulus or compound as a taste enhancer, that may be added to food products to enhance their taste. A candidate modifier that results in a decreased magnitude of response, slower latency, or shorter response duration to the target stimulus is identified to be useful as a masking, blocking or suppressing agent of the target stimulus. If results show no difference in the response to the target stimulus in the presence versus absence of the candidate modifier, the compound is not a modifier for the target stimulus.

Determination of Differences in the Taste Cell Response in Different Test Subjects:

The response to a given stimulus (e.g. known tastant, known tastant and taste modifier) of taste cells derived from different sources is compared. By employing these assays it can be determined whether the cellular responses to a stimulus or tastant differ between different sources of taste cells that are selected according to different cultures, individuals, species or in correlation with differences in age, genetic composition, metabolic or nutritional status, disease state, medication use, and therapeutic treatment.

The identified differences allow development of improved taste systems targeting flavors and flavor compositions, e.g. for food products, which are tailored to the needs of specific species, populations or individuals. For example, reduced responsiveness to a particular stimulus in cells derived from elderly versus young subjects would identify a necessary increase/decrease in the stimulus concentration to improve the taste quality for consumers depending on the age of the consumer group for which the product is intended. The efficacy of a taste modifier whose activity is known in one species may be identified in a different species to identify taste stimuli efficient in the species of interest.

Assays Based on Cellular Response of Taste Cells Relating to Different Cellular Parameters:

Parameters measured include differences in response as detailed above, the frequency of responses to taste stimuli, or specified cellular parameters including proliferation rates of cells, expression, of protein markers relevant for taste or taste cell regeneration (proliferation, differentiation, survival), and others as described in the Examples.

Candidate compounds that influence taste cell regeneration, repair, proliferation, differentiation, survival and replacement, that may be useful as therapeutic drugs, can be identified by the comparison of the taste cell response in the presence and absence of a candidate compound. Cells may be exposed to candidate compounds either in vivo or in vitro.

Candidate stimuli or compounds identified by the above-described assays may be validated further by one or more of the following methods as is well known in the art. These include behavioral testing with test subjects, sensory testing, signal transduction testing, physiological methods (for example nerve recording), as described for example by Spielman. A. I., Brand, J. G. (Editors), "Experimental Cell Biology of Taste and Olfaction", CRC Press, Boca Raton, Fla., pp. 437, 1995, and Doty, R. L. (Ed.): Handbook of Olfaction and Gustation, 2nd edition N.Y.: Marcel Dekker, 2003, 1150 pp.

Stimuli or compounds identified by assays employing taste cells according to the invention may be added to food products. "Food products" are meant to include all products applied in the oral cavity, including medicaments, mouthwash and other oral health and hygiene products. Further it includes pet food products.

Transfection Methods

The present invention for the first time provides transfected cultured taste cells. In another of its aspects, the invention is therefore directed to cultured taste cells, preferably taste cells cultured according to the present invention, transfected, for example, by a plasmid vector, and to methods of producing such cells, for example by transfection, for example, by employing plasmid vectors.

Taste cells, including taste cells and taste receptor cells cultured according to the methods of the present invention, may be transfected using standard methods for transfection of eukaryotic cells, for example as described by Murray, E J, editor (1990), Gene Transfer and Expression Protocols: Methods in Molecular Biology, Vol. 7, Humana Press, Clifton, N.J.; Perkus M E et al. (1993, *J. Tiss. Cult. Meth.* 15: 72); Feigner, J. et al. (1993, *J. Tiss. Cult. Meth.* 15: 63). Alternatively, they may be transfected using the FuGene® 6 Transfection Reagent (Roche Diagnostics, Basel, Switzerland), as shown for an expression vector containing a reporter gene in Example 10. Taste cells according to the invention can also be transfected virally by employing known methods of viral transfection as is well known in the art. Methods for introducing genetic material into taste cells using a virus are known (Kishi et al., 2001, *Neuroscience* 106 (1): 217-25; Stone et al. 2002, *Chem. Senses* 27: 779-87).

Plasmid vector transfection protocols have the advantage that complicated virus handling is avoided. Taste cells according to the invention can be successfully transfected with good transfection efficiency with plasmid vectors resulting in fluorescent signals from transfected proteins (such as Green Fluorescent Protein) that are easily visualized. Using cultured cells according to the invention, a good transfection efficiency may be one of at least about 10%, preferably at least about 20%, more preferably of at least about 50%. Preferably, cells cultivated for at least about 5 days or longer (for example at least about 7 days, at least about 2 weeks, at least about 3 weeks, at least about 4 weeks, and at least about 2 months) are used.

The following examples describe several aspects of embodiments of the invention in greater detail. These examples are provided to further illustrate, not to limit, aspects of the invention described herein.

EXAMPLES

Example 1

Isolation of Taste Cells Including Taste Receptor Cells from the Rat Taste Papillae (Circumvallate, Foliate) and Cell Culture Employed rats are 1-2 month old adult male Sprague-Dawley rats. Rats are sacrificed by $CO_2$ inhalation followed by cervical dislocation. The tongue is dissected proximal to circumvallate papillae and immediately placed into a cold isolation solution (26 mM $NaHCO_3$, 2.5 mM $NaH_2PO_4$, 20 mM glucose, 65 mM NaCl, 20 mM KCl, and 1 mM EDTA) for 5 to 10 minutes on ice.

The preparation is removed from ice and about 1 ml of the isolation solution is mixed with 1.5 ml/ml pronase E (Protease from *Streptomyces griseus*, commercially available from Sigma, St. Louis, Mo., USA, product no. P 6911, with an activity of 5.5 units/mg solid. Unit definition: 1 U will hydrolyze casein to produce color equivalent to 1.0 micromole (181 microgram) of tyrosine per minute at pH 7.5 at 37° C.) and 1 mg/ml elastase (also called pancreatic porcine pancreas Type I, CAS Number 39445-21-1, commercially available from Sigma, Saint Louis, Mo., USA, Prod. No. E1250, aqueous suspension with 4 units/mg protein).

The resulting solution with enzymes is uniformly injected with a 25 gauge NORM-JECT® syringe under and around the lingual epithelium of circumvallate and foliate papillae of the dissected tongue, which is swollen to about twice its normal size. The dissected tongue with enzyme solution is placed in cold isolation solution and incubated 15 minutes at room temperature.

After the enzyme incubation, the epithelium is gently peeled from the underlining muscle layer under the dissecting microscope (Stereomaster, Fischer Scientific, Pittsburgh, Pa.) and soaked in isolation solution. The epithelium from the region of the circumvallate and foliate papillae is isolated and transferred to the culture medium.

The following culture media are employed:

Iscove's medium ("Iscove's Modification of DMEM" from CELLGRO® by Mediatech Inc, Herndon, Va., USA, Product No. 10-016) containing 10% Fetal Bovine Serum (BTI, MA, USA), 15-20% MCDB 153 medium (Sigma, Saint Louis, Mo., USA), 10 ng/ml Insulin and antibiotics (100 U/ml/100 µg/ml Penicillin/Streptomycin, 2.5 µg/ml Gentamycin and 0.5 µg/ml Fungizone).

Dulbecco's modified Eagle's medium (DMEM) (Gibco BRL, NY, USA; Cellgro, USA) with or without 10% FBS MCDB 153 (Sigma, Saint Louis, Mo., USA)

In the medium, the isolated epithelium from the region of the circumvallate and foliate papillae is minced into small pieces with the surgical scissors, so that both whole taste buds and partially dissociated taste buds are present. The pieces of epithelium are seeded onto the selected culture dishes or cover slips. The different culture dishes or cover slips that are employed are:

rat tail type 1 collagen-coated (3.96 mg/ml diluted 1:4 in water, BD Sciences, San Diego, Calif.) 18 mm round glass coverslips (Fisher, USA);

Polystyrene culture dishes without coating;

Glass coverslips without coating;

Glass coverslips coated with matrix gel (2 ml/l, ATCC, USA). The matrix solution is prepared from the Engelbreth-Holm-Swarm (EHS) mouse sarcoma (ATCC, USA, Prod. No. CRL-2108). Matrix gel is employed in three variants as follows: Cells are embedded within matrix gel before seeding and gently applied on coverslip; coverslip is coated with matrix gel and cells are seeded on the polymerized matrix gel; cells are seeded onto matrix gel while the gel is polymerizing;

Glass coverslips coated with poly-D-lysine (Sigma, Saint Louis, Mo., USA, Prod. No. P-6407, Final working concentration is 0.1 mg/ml).

Before coating or use, coverslips are treated as follows: Incubation in 2M NaOH for 1 hour and incubation overnight in 70% nitric acid ($HNO_3$), followed by incubation for 1 hour in an HCl acid wash. Then the coverslips are autoclaved in water, rinsed with 70% ethanol and 100% ethanol, and air dried.

The culture dishes or cover slips are incubated at 37° C. in a humidified environment (95% humidity) containing 5% $CO_2$. The culture medium is replaced after 24-48 hours and then every 5-10 days.

Adherence of cells is monitored using a microscope (10×) after overnight culture.

The viability of cells is determined by staining with Trypan Blue (Sigma, Saint Louis, Mo., USA). Trypan Blue is added to the culture dish at a concentration of 0.2% (w/v). After 5 to 10 minutes, 100 cells are counted under a phase contrast microscope at 10×magnification using an ocular grid. Dead cells are recognizable by their blue-stained nuclei under a phase contrast microscope. An area of the cell culture dish or coverslip is photographed and the viability of cells (viable cells counted divided by total cells counted, multiplied by 100) is determined by counting 100 cells for each of 2-3 coverslips.

Results:

Cells are monitored during the entire culturing period and show the following characteristics when kept using the isolation procedure, collagen-coated culture surfaces and Iscove's culture medium according to the invention:

Individual cells and bud type cells are visible 24-48 hours after plating. Cells grow in form of attached cells and cell clusters for up to day 7-8. After day 5-7, cell clusters which give rise to daughter cells start to detach. Cells maintain their original shape up to day 15-20. After day 15-20, part of the cell population starts to change morphology, though the cells maintain their compact appearances retaining round cell bodies with or without one or more processes. After 20 days, most of the long term cultured cells gain a flatter appearance. Cells maintain a high viability for up to 3 weeks with at least 95% viability, in most dishes at least 98% to 99% viability.

When using another isolation protocol or different cell culture surfaces without collagen, cells either do not attach, or if they are cultured the number of dead cells increases rapidly at 2 weeks at latest.

The percentage of cell attachment is determined after overnight culture. When cells are isolated as described above, seeded on collagen-coated coverslips, and cultured in Iscove's medium+20% MCDB 153+10% FBS+10 ng/ml insulin+antibiotics (Penn/Strep+Genta+fungizone), cells show a cell attachment rate after overnight incubation (12-16 hours) of 15-20%. After 7 days, the cells are found at least 90% viable. After 2 months, the cells are still at least 90% viable.

TABLE 1

Culture dish/cover slip surfaces (cells isolated with the improved protocol according to the invention and cultured in Iscove's medium)

| Surface/coating | Primary Cells attached [%] | Viability after 20 days |
| --- | --- | --- |
| Polypren/Polystyren without coating | 0% | — |
| Glass coverslip without coating | 0% | — |
| Matrix Gel coating on glass coverslip | 3-5% | — |
| Poly-D-lysine on glass coverslip | 0% | — |
| Rat Tail collagen on glass coverslip | 15-20% | At least 90% |

TABLE 2

Tissue culture media (cells isolated with the improved protocol according to the invention and seeded on collagen coated coverslips)

| Tissue Culture Medium | Primary Cells attached [%] | Viability of cells at day 14 | viability of cells at day 20 or more |
| --- | --- | --- | --- |
| DMEM | 0 | — | — |
| MCDB 153 | 0 | — | — |
| Iscove's medium | 5-10% | Viable (at least 90%) | 80-90% |
| Iscove's medium + 20% MCDB 153 + 10% FBS + 10 ng/ml insulin + antibiotics (Penn/Strep + Genta + fungizone) | 10-15% | Viable (at least 98-99%) | at day 28: 98-99%, at month 2-3: 95%; |

Isolated with the enzymes indicated, on the optimized surface and with the optimized medium, taste cells are maintained for at least up to 2 months, up to 3 months, and potentially longer. The first 3 to 4 weeks the taste cells maintain a viability near about 98 to 99% as tested with Trypan Blue as described above. After 2 months and at 3 months, the taste cells still maintain a viability of about 95% and part of the cells proliferate.

Example 2

Proliferation of Taste Cells Including Taste Receptor Cells Shown by BrdU Labelling To determine whether primary cell cultures contain proliferative cells, 5-bromo-2-deoxyuridine (BrdU) incorporation is performed as described below for cultures up to 11 days old.

60-70 percent of the taste cells are found labeled with BrdU, which shows that the taste cells continue to proliferate after a culture duration of at least up to 11 days when isolated by the protocol of Example 1 and cultured as detailed below.

Taste cells are isolated from rat as described in Example 1 and seeded in collagen-coated coverslips. The cells are cultured for 5-6 days and then treated with 50 µM BrdU (Sigma, Saint Louis, Mo., USA) dissolved in 10 mM DMSO for 24-48 hours, after which BrdU is removed by replacement of the medium with Iscove's medium+20% MCDB 153+10% FBS+10 ng/ml insulin+antibiotics (Pen/Strep+Genta+fungizone). The cells are maintained for 3 more days in culture on coverslips and then fixed with 4% paraformaldehyde in 0.1 M PB (pH 7.2) for 10 minutes at room temperature. After fixation, cells are analyzed for BrdU incorporation by immunohistochemistry. After fixation, coverslips are washed three times (5 minutes each) in 0.1 M PBS (pH 7.2), and treated with $H_2O_2$ solution (4 mL phosphate buffered saline (PBS)+ 0.5 mL 100% methanol+0.5 mL 30% $H_2O_2$) for 20 minutes at room temperature to block endogenous peroxidases. Afterwards the coverslips are rinsed with PBS, then denatured with 2 N HCl at 37° C. for 30 minutes. After denaturation, the coverslips are washed with PBS, and incubated with blocking buffer in PBS (SuperBlock®, Pierce Chemical Company, Rockford, Ill.) for 1 hr at room temperature to reduce nonspecific binding. Then the coverslips are incubated overnight with mouse anti-BrdU (diluted 1:100, Sigma, Saint Louis, Mo., USA B-2531) diluted in 10% SuperBlock with 0.05% TWEEN20 at 4° C. After three washes in PBS, the coverslips are incubated with FITC-conjugated anti-mouse IgG (1:500, Santa Cruz Biotechnology) diluted in 10% SuperBlock with 0.05% TWEEN20 for 1 hr at room temperature. Afterwards, coverslips are washed three times in PBS for 5 minutes each, and washed three times for 10 minutes each in water. Finally coverslips are mounted with a mounting medium (Vectashield®, or Vectashield® with DAPI, Vector Labs, USA).

As a negative control, mouse IgG control sera is used in place of the primary antibody to exclude non-specific staining of BrdU by the anti-BrdU antibody. As further confirmation, unlabeled cells are stained with anti-BrdU antibody. None of these controls indicates any specific staining related to BrdU and the BrdU staining of the taste cells is found to be specific.

Example 3

Expression of Taste Cell-Specific Markers by RT-PCR

Reverse Transcription-Polymerase Chain Reaction (RT-PCR) analysis is performed on taste cells isolated and cultured as described in Example 1 according to the fast isolation procedure and cultured on collagen-coated culture dishes and in Iscove's medium modified as described in Example 1.

The following taste cell specific markers are analyzed by RT-PCR: gustducin, PLC-beta-2 (PLC-β2), TRAMS, T1R3, and T2R5. Beta-actin (a housekeeping gene) is used as a positive control.

Total RNA is isolated from taste cells cultured for 7-10 days, taste cells cultured for 2 months, and as a positive control, from rat tongue epithelium. RNA is isolated, reverse transcribed and amplified by PCR as described below. In all samples (cultured taste cells 7-10 days, 2 months, and rat tongue epithelium), the amplification product of the expected size is detected. This shows that cultured taste cells continue to express mRNA of taste cell-specific markers even after 2 months of culture.

Protocol Used for RNA-Isolation, Reverse Transcription and Amplification by PCR:

Each sample is extracted with TRIZOL reagent (Invitrogen Corp, USA) as is well-known in the art, for example according to manufacturer's instructions. Alternatively, RNA may be isolated, reverse transcribed and amplified as described by Maniatis et al., 1982, "Molecular Cloning, A laboratory Manual", Cold Spring Harbor Laboratory.

A total 20 μl volume of 4 μg RNA is reverse transcribed for 90 minutes at 42° C. using the SUPERSCRIPT First Strand Synthesis System for RT-PCR (Invitrogen Corp., USA). As a negative control to check genomic DNA contamination, samples of RNA are treated in parallel in the presence and absence of reverse transcriptase and used for PCR. Later tests for genomic DNA contamination by PCR amplification show that there is no genomic DNA contamination. The known specific primers used to show expression of gustducin, PLC-β2 beta-actin, T2R3, T1R5, and TRPM5 are listed below.

Primers are chosen to span one or more introns to exclude confusion with amplified fragments from genomic DNA and ensure the generation of a target-specific product. Primers for gustducin, PLC-β2, and β-Actin were published previously, for example in Rossler et al. 2000, *Chemical Senses* 25: 413-421. TRPM5 was published previously by Heiner et al. 2003, *Biochem. J.* 371: 1045-1053. The primer first indicated is the forward primer, the second is the reverse.

Gustducin:

(SEQ ID NO: 1)
5'-gat gct agc caa tcc gag aag tag aga gg-3',
(SEQ ID NO: 2)
5'-cgg aga tct gct gtt gaa gag gtg aag ac-3';

PLC-β2:

(SEQ ID NO: 3)
5'-ctg gag gct gaa gta aag gag-3',
(SEQ ID NO: 4)
5'-gcc cct gca tgt atg tta gg-3';

β-Actin:

(SEQ ID NO: 5)
5'-tca tgt ttg aga cct tca a-3',
(SEQ ID NO: 6)
5'-gtc tt gcg gat gtc cac g-3';

T2R5:

(SEQ ID NO: 7)
5'-tgg caa atc cac atg aag aa-3',
(SEQ ID NO: 8)
5'-gca ggg ata gag gaa tgc aa-3';

T1R3:

(SEQ ID NO: 9)
5'-gat cag tgg tcc cca gaa aa-3',
(SEQ ID NO: 10)
5'-taa gct agc atg gcg aag gt-3';

TRPM5:

(SEQ ID NO: 11)
5'-caa gat cat cgt ggt aga gc-3',
(SEQ ID NO: 12)
5'-tcc aga aca tgt ctg cgt tg-3'.

PCR amplification of cDNA for each RT reaction is performed in a final volume of 50 μl containing 2 μl of RT reaction, 1× Ampli Taq Gold® PCR buffer, 2.5 mM MgCl$_2$, 1 mM deoxynucleoside triphosphates, 0.4 μM of each primer, and 0.25 U/μl of Ampli Taq Gold® polymerases (Applied Biosystems, Foster City, Calif.). PCR amplification consists of initial denaturation at 95° C. for 5 min followed by cycles of denaturation at 94° C. for 30 sec, annealing at 55° C. for 45 sec, and extension at 72° C. for 30 sec. After 40 cycles of amplification, the final extension is at 72° C. for 10 min. PCR products are separated on 1.4% agarose gels and stained with 0.2 μg/ml of ethidium bromide to verify their expected size.

Example 4

Immunohistochemical Localization of Taste Receptor Cell-Specific Biomarkers Gustducin, PLC-β2 and BrdU α-gustducin and PLC-β2 are known biomarkers for differentiated taste receptor cells that respond to taste stimuli. BrdU is a general marker for cell proliferation. Immunocytochemistry is performed on cultured taste cells isolated and cultured as described in Example 1 according to the fast isolation procedure and cultured on collagen-coated culture dishes and in Iscove's medium modified as described in Example 1. Taste cells analyzed are cultured for 7-10 days, or for 2 months, and are tested for their immunoreactivity for α-gustducin, PLC-β2 and BrdU as described in the protocol below. Antibody specificity is confirmed by using antibody-specific immunoglobulin to detect non-specific binding. Immunostaining with antibody-specific immunoglobulin demonstrates the absence of non-specific immunostaining.

Immunoreactivity for both α-gustducin and PLC-β2 is observed both in 7-10 days and in 2 month old cultures, with a similar expression pattern, i.e. they are expressed in cells of similar morphology.

Protocol for Immunoreactivity:

Cells seeded on collagen-coated coverslips are fixed using 4% paraformaldehyde in 0.1 M phosphate buffer (pH 7.2, PB) for 10 minutes at room temperature. After three washing steps (duration 10 minute each) in phosphate-buffered saline (PBS), the coverslips are blocked with 0.3% Triton X-100, 2% normal goat serum, and 1% bovine serum albumin in 0.1 M PBS for 1 hour followed by another three washes in PBS. Primary antibody diluted in blocking solution is added to the coverslips and incubated overnight at +4° C. Primary antibodies used were polyclonal rabbit anti-gustducin (dilution 1:500-1:1000) and polyclonal rabbit anti-PLC-$\beta$2 (dilution 1:1000, Santa Cruz Biotechnology). Coverslips are then washed in PBS and reacted in the dark with ALEXA FLUOR 488 anti-mouse (1:500, Molecular Probes Inc.) or ALEXA FLUOR 633 anti-rabbit (1:500, Molecular Probes Inc.) diluted in blocking buffer for 1 hour at room temperature. After the final PBS and water washes, coverslips are mounted with VECTORSHIELD.

All double immunolabeling studies are done in a similar manner except that the second primary antibody, anti-gustducin or anti-PLC-$\beta$2, is introduced after detection of the first primary antibody anti-BrdU is completed. Controls for immunofluorescence microscopy consist of omitting the primary antiserum and no immunoreactivity is seen under these conditions.

Example 5

Immunohistochemical Localization of Gustducin, PLC-$\beta$2, and BrdU in Parallel The relationship between cells that have proliferated in vitro and taste cells' specific biomarker expression is analyzed in parallel by double labelling with gustducin, PLC-$\beta$2, and BrdU. The experiments are performed as described in Example 4, each with two of the three biomarkers in parallel.

Taste cells cultured for 7-10 days and 2 months exhibit expression of specific markers for differentiated taste cells (gustducin, PLC-$\beta$2) as well as proliferation (the latter is shown by BrdU staining). Experiments are performed by double labelling with gustducin or PLC-$\beta$2, each combined with BrdU. While some cells show signals for only one of each marker (either BrdU, gustducin, or PLC-$\beta$2), the large majority of cells show signals for two of the markers in parallel (gustducin and BrdU, PLC-$\beta$2 and BrdU). This shows that cells have both proliferated and differentiated into taste cells in vitro.

Example 6

Confocal Imaging

Fluorescent images are captured with the Leica TCS SP2 Spectral Confocal Microscope (LEICA Microsystems Inc., Mannheim, Germany) using UV, Argon and HeNe lasers. The coverslips are viewed under a HC PL APO CS 20.0x (0.070 NA) objective. Excitation wavelengths used are 405 nm for DAPI, 488 nm for ALEXA FLUOR 488, and 633 nm for ALEXA FLUOR 633 with emissions detected at appropriate wavelengths. The pinhole diameter is set at the first minimum diameter of the Airy disc for the objective used, giving acceptable resolution of the z-axis for the fluorescent focal plane. The power for the laser beam and gain of the photomultiplier are adjusted to optimize the signal/noise ratio. Sequential acquisition of each wavelength are used for some double labelling experiments and showed no signal bleed across the wavelength or differences when compared with simultaneous scans. LEICA Scanware software is used to acquire confocal images scanning unidirectionally at a 1024×1024 pixel format with 2 lines plus 3 frames averaging. Computer controlled digital zoom is used to increase magnification to a maximum of 2.5× under 20× objectives. Digital images are arranged and adjusted for contrast and brightness using LCS software (LEICA Microsystems Inc.).

Example 7

Expression of Taste Receptor Cell-Specific Markers Analyzed by Western Blot

For gustducin and PLC-$\beta$2 expression of cultured taste cells, Western Blots are employed according to the protocol described below.

Cultured taste cells tested are cultured for 1 week and 2 months as described in Example 1 on collagen-coated culture dishes with Iscove's medium modified according to the invention as described in Example 1.

These cells are tested for their expression of the differentiated taste cell-specific biomarkers gustducin and PLC-$\beta$2. As a positive control, samples obtained from freshly isolated rat tongue foliate and circumvallate tissue lysate are used. Gustducin and PLC-$\beta$2 expression is shown in all samples. For PLC-$\beta$2, using anti-PLC-$\beta$2 antibodies, two distinct bands are shown that had been previously reported (Wei and Neer 2001, *J. Biological Chemistry* 276, pp. 2503-2508). For both biomarkers, the positive control has a stronger signal and expression level compared to the cultured cells. Between cells cultured 1 week or 2 months, there are no differences in signal level. Taste cells isolated and cultured as described in Example 1 maintain their specific biomarkers for at least 2 months.

Western blots are conducted using standard immunoblotting techniques well-known in the art, for example by Maniatis et al., 1982, "Molecular Cloning, A laboratory Manual", Cold Spring Harbor Laboratory.

Cultured primary rat taste cells (7-10 days and 1-2 months old) are lysed in and tissue samples from rat circumvallate and foliate papillae are homogenized in RIPA (150 mM NaCl, 10 mM Tris pH 7.2, 0.1% SDS, 1% Triton X-100, 1% Deoxycholate, 5 mM EDTA) buffer containing protease inhibitors (104 mM AEBSF, 80 $\mu$M Aprotinin, 2 mM Leupeptin, 4 mM Bestatin, and 1.5 mM Pepstatin A). The protein concentration is estimated for each sample using Bio-Rad Dc Protein estimation kit (Bio-Rad Laboratories, Hercules, Calif.) as is well-known in the art, for example, according to the manufacturer's protocol. Protein samples are mixed with SDS loading buffer containing beta-mercaptoethanol, boiled for 5 minutes, and then placed on ice for 5 minutes. The cellular homogenates are separated by SDS-polyacrylamide (5-15%) gradient gel (Bio-Rad Labs.) electrophoresis and transferred to a PVDF membrane (Bio-Rad Labs) that is incubated at 4° C. overnight with 1% of nonfat dry milk. Polyclonal rabbit anti-gustducin (Antibody gustducin 1-20, Santa Cruz Biotechnology, Santa Cruz, Calif., product No. sc-395) (dilution 1:1000) and polyclonal rabbit anti-PLC-$\beta$2 (Santa Cruz Biotechnology, Santa Cruz, Calif.) (dilution 1:1000) are used to identify taste cells. After 1.5 hr incubation with these primary antibodies at room temperature, the membrane is washed and rinsed 3 times by incubating for 15 minutes each in 0.1M phosphate buffer solution with 0.05% TWEEN20 ("PBS/T"), reacted for 1 hour at room temperature with HRP-conjugated secondary anti-rabbit antibody (dilution 1:5000, NA 934, Amersham). The membrane is washed and rinsed 3 times by incubating for 15 minutes each in a large volume of PBS/T. Signals are detected with the enhanced chemiluminescence (ECL) immunoblot detection system (Amersham Biosciences, Piscataway, N.J.) as is well known in the art, for example according to manufacturer's instructions. X-rays films are later scanned with a scanner for analysis.

Example 8

Response of Taste Cells to Different Taste Stimuli Determined by Ca-Imaging Taste cells employed are isolated as described in Example 1 and cultured for 1 week or 2 months on rat tail collagen type 1-coated coverslips.

Ca-imaging is performed as follows. The coverslips are incubated for 15-30 minutes with calcium sensitive dye in Modified MHNK ringer's solution (80 mM NaCl, 5 mM KCl, 1 mM $MgCl_2$, 1 mM $CaCl_2$, 1 mM Na-pyruvate, and 20 mM Hepes-Na, pH 7.2 with osmolarity adjusted to 300-310 by 5M NaCl) supplemented with 1 mM Fura-2 AM (Molecular Probes Inc., Eugene, Oreg.) and 20 mg/ml PLURONIC F127 (Molecular Probes Inc.). The calcium sensitive dye fura-2 AM is cleaved to fura-2 which is fluorescent and can be detected.

After incubation, coverslips are placed in a recording chamber and continuously bathed with Modified MHNK Ringer's solution that is applied as superfusion.

The stimuli (Denatonium benzoate 2 mM and 0.5 mM, Acesulfame K 250 ppm, Monosodium glutamate (MSG) 3 mM, Cycloheximide 25 µM, Glycine 125 mM, and High K buffer (modified Modified MHNK ringer's solution with 5 mM NaCl, 80 mM KCl, 1 mM $MgCl_2$, 1 mM $CaCl_2$, 1 mM Na-pyruvate, and 20 mM Hepes-Na, pH 7.2 with osmolarity adjusted to 300-310 by 5M NaCl) are applied to the coverslip by switching the superfusion to the stimulus solution, which allows for a complete change of bath solutions in the chamber within 10 seconds.

Calcium imaging recordings are performed using standard imaging techniques as described by Restrepo D., M. Zviman and N. E. Rawson, "The measurement of intracellular calcium in chemosensory cells", in: Methods in Chemosensory Research, Ed. by A. Spielman and J. Brand. CRC Press, 1995. Illumination is provided by a LSR SPECTRAMASTER monochromator coupled to the microscope. Emitted light from fura-2 in the cells under 200× magnification is filtered at 510 nm and recorded with a cooled CCD camera (Olympix, Perkin Elmer Life Sciences, Bethesda Md.). The excitation wavelength is 340-380 nm and the emission wavelength is 510 nm using a wide band filter. Images are digitalized using a Merlin Imaging Workstation (Perkin Elmer Life Sciences, Bethesda Md.), which controls illuminator, camera, and acquisition, and performs the image ratioing and the display of pseudocolor images. After introduction to the recording setup, cells remain viable for over 2 days and can be imaged continuously for 2 hours at a time without visible effects of dye bleaching.

Stimuli are diluted in Modified MHNK ringer's solution and applied via a gravity-flow superfusion apparatus for about 10-60 seconds, depending on the stimulus. Cells can be stimulated by all stimuli tested as shown by a positive signal for Fura-2 AM for at least one cell selected. Typically several cells are tested.

Example 9

Maintenance of Taste Cells in Improved Buffer for Assays

Cultured taste cells employed are as described in Example 8. Cultured taste cells on coverslips are incubated overnight in an improved assay buffer outside of the incubator at room temperature (22-25° C.). The improved assay buffer is modified MHNK ringer's solution (80 mM NaCl, 5 mM KCl, 1 mM $MgCl_2$, 1 mM $CaCl_2$, 1 mM Na-pyruvate, 20 mM Hepes-Na, pH 7.2) with the osmolarity adjusted to 300-310 by 5 M NaCl.

In this assay buffer and under the above incubation conditions, the cells are maintained for up to 24 hours and still respond to the stimuli (compare Example 10 for stimuli applied) as determined by positive Fura-2 AM signal (performed as described in Example 8). Cells show the same results compared to 24 hours before examination. When exposed to higher osmolarities of 320 or higher, cells die and do not stain with fura-2 AM. This maintenance of primary taste cell cultures in assay buffer is useful for assay purposes.

Example 10

Transfection of Cultured Taste Cells

Taste cells isolated as described in Example 1 cultured onto collagen-coated-coverslips are transfected at day 5-7 after isolation with 5-8 µg pGFP2-MCS-Rluc (h) expression vector (BioSignal Packard, Montreal, Canada, Product No. 6310051) and FuGene® 6 Transfection Reagent (Roche Diagnostics, Basel, Switzerland) according to the Roche Diagnostics "FuGene 6 Transfection Reagent" Instruction Manual, Version 5, September 2000. 15-24 microliters of Fugene 6® Transfection Reagent are added to 50 microliters serum-free medium. The medium that is used is supplemented Iscove's medium as described in Example 1 except that it is serum-free. The mixture is mixed by hand gently. Five to eight micrograms DNA (pGFP2-MCS-Rluc (h) expression vector) are added, and the mixture is mixed by hand gently. The mixture is incubated at room temperature for 15-30 minutes and then added dropwise onto the cells. The plate is swirled gently and incubated at 37° C. in a cell culture incubator for 2 days.

Alternatively, cells may be transfected using standard methods for transfection of eukaryotic cells, as is well known in the art, for example as described by Murray, E J, editor (1990), Gene Transfer and Expression Protocols: Methods in Molecular Biology, Vol. 7, Humana Press, Clifton, N.J.; Perkus M E et al. (1993, *J. Tiss. Cult. Meth.* 15: 72); Feigner, J. et al. (1993, *J. Tiss. Cult. Meth.* 15: 63).

After 24-48 hours, cells are fixed in 4% paraformaldehyde (PFA) in PBS for 10 minutes and fluorescent signals of Green Fluorescent Protein (GFP) are detected by confocal microscopy. Expression of GFP is easily visualized.

This shows that taste cells according to the invention provide a feasible expression system in a system more similar to in vivo than the cell lines typically used. Similar to the test-DNA used (pGFP2-MCS-Rluc (h) expression vector), DNA of taste receptors may be over-expressed.

Example 11

Transfection of Cultured Taste Cells with mT2R5 and hT2R16 and Calcium Imaging Transfection in Example 11 is performed as described in Example 10 subject to the following modifications:
the coverslips used are rat tail collagen-1-coated coverslips;
transfection is performed at day 3-7 after isolation; and
transfected DNA is the expression vector of Example 10 with GFP or an expression vector carrying a DNA insert, either mouse T2R5DNA (sst:mT2R5:HSV/pcDNA3.1-zeo, 6053 bp) or alternatively, human T2R16 DNA as insert (in both cases, the construct may be formed as described for the cloning of the human TAS2R genes by Bufe et al. *Nat Genet.* 2002 November; 32 (3):397-401).

Expression is detected in cultured taste cells using antibodies against tag protein (Herpes Simplex Virus Glycoprotein D, HSV-D). Transfected and untransfected cells are incubated overnight at 4° C. with an antibody against gustducin (rabbit polyclonal anti-gustducin, (Santa Cruz, 1:1000), washed with PBS (3 times, 15 min. each), and then incubated for 30 min at room temperature with goat anti-rabbit ALEXA-633 (Molecular Probe, 1:500), washed with PBS (3 times, 15 min each), and then incubated with the mouse anti-HSV-Tag Monoclonal antibody (Novagen #69171-3, 1:1000) overnight at 4° C., washed with PBS (3 times, 15 min. each), then incubated with goat-anti-mouse ALEXA 488 (Molecular Probe, 1:500) for 30 minutes at room temperature. Coverslips are then washed three times in PBS for 10 minutes each, and three times for 10 minutes each in water, mounted with a mounting medium (Vectashield®, or Vectashield® with DAPI, Vector Labs, USA) and viewed on a confocal or epifluorescence-equipped microscope. Controls for non-specific immunoreactivity include omitting the primary antibodies and substitution of the primary antibodies with rabbit and mouse IgG, in which case no immunostaining is detected.

Both GFP, and HSV-D tag probes show strong fluorescence signals indicative of over-expression. The signal for HSV-D tag immunofluorescence is correlated with the expression of T2R5 or T2R16 protein, respectively. These results demonstrate that the cultured taste cells according to the invention provide a feasible expression system.

Alternatively, transfected cells are used for calcium imaging assays as described in Example 8. Cells transfected with T2R5 as described exhibit an increase in intracellular calcium in response to cycloheximide at effective concentrations of 1 microM cycloheximide, which is comparable to the concentration observed in HEK293 cells transfected with this receptor by Ueda et al., *J. Neurosci.*, 2003. 23 (19):7376-7380.

Cells transfected with T2R16 as described exhibit an increase in intracellular calcium in response to phenyl-beta-D-glucopyranoside at an effective concentration of 1 milliM which is comparable to the concentration observed in HEK293 cells transfected with this receptor by Bufe et al *Nat Genet.* 2002 November; 32 (3):397-401.

Again, these results demonstrate that the cultured taste cells according to the invention provide a feasible expression system.

It should be appreciated that the present invention is not limited to the specific embodiments described above, but includes variations, modifications, and equivalent embodiments defined by the following embodiments. Further, all embodiments disclosed are not necessarily in the alternative, as various embodiments of the invention may be combined to provide the desired characteristics.

What is claimed is:

1. A method for generating a mammalian taste receptor cell culture comprising:
    contacting mammalian tongue epithelium tissue with proteolytic enzymes, thereby yielding enzyme-exposed tongue epithelium;
    culturing said enzyme-exposed tongue epithelium tissue on a collagen-coated surface in culture medium, wherein said culture medium comprises Iscove's medium; and
    replacing culture medium at about 24 to 48 hours and then every about 5 to 10 days, thereby generating a mammalian taste receptor cell culture.

2. The method of claim 1 wherein said proteolytic enzymes comprise pronase E and elastase.

3. The method of claim 1 wherein the length of said contacting is about 30 minutes or less.

4. The method of claim 1, wherein said proteolytic enzymes are added to an isolation solution.

5. The method of claim 4 wherein said isolation solution comprises $NaHCO_3$, $NaHPO_4$, NaCl, KCl, and EDTA.

6. The method of claim 1 wherein said culture medium is supplemented with 15-20% MCDB 153 medium, 10% fetal bovine scrum, 10 ng/ml insulin, and antibiotics.

7. The method of claim 1 wherein the tongue epithelium tissue is isolated from the region of the circumvallate and foliate papillae.

8. The method of claim 1 further comprising mechanically digesting said tongue epithelium tissue prior to said contacting.

* * * * *